Figure 1:
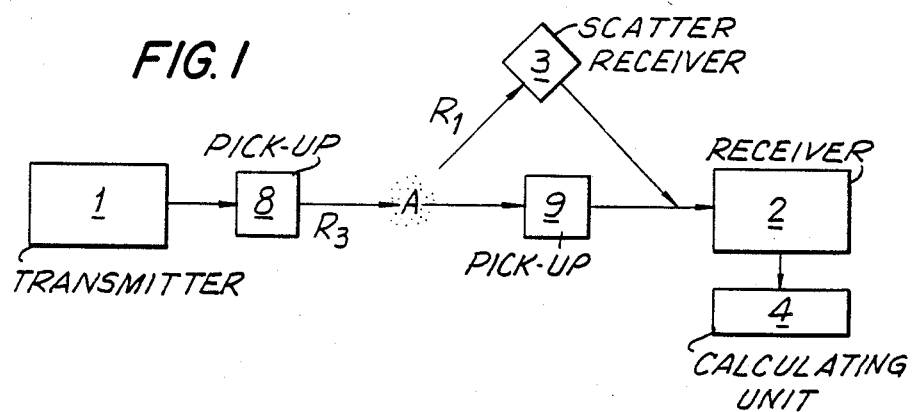

United States Patent [19]

Karras et al.

[11] Patent Number: 4,911,013

[45] Date of Patent: Mar. 27, 1990

[54] PROCEDURE AND APPARATUS FOR ANALYZING PULP SLURRY

[76] Inventors: Matti Karras, Haapanantie 36, SF-90150 Oulu; Arto Kemppainen, Tapiontie 3 A 2, SF-90570 Oulu; Eino Härkönen, Mielikintie 6 B 13, SF-90550 Oulu; Jouni Tornberg, Kumputie 28, SF-87200 Kajaani, all of Finland

[21] Appl. No.: 290,869

[22] Filed: Dec. 28, 1988

Related U.S. Application Data

[63] Continuation of Ser. No. 137,277, Dec. 22, 1987, abandoned, which is a continuation of Ser. No. 915,817, Oct. 6, 1986, abandoned.

[51] Int. Cl.[4] .................. G01N 15/06; G01N 29/00
[52] U.S. Cl. ............................. 73/599; 73/61 R
[58] Field of Search .................. 73/570, 61 R, 599

[56] References Cited

U.S. PATENT DOCUMENTS

| | | | |
|---|---|---|---|
| 2,966,056 | 12/1960 | Heller | 73/61 R |
| 3,974,683 | 8/1976 | Martin | 73/61 R |
| 4,412,451 | 11/1983 | Uusitalo et al. | 73/599 |
| 4,527,420 | 7/1985 | Foote | 73/61 R |
| 4,542,644 | 9/1985 | Clayton et al. | 73/61 R |
| 4,667,515 | 5/1987 | Farren et al. | 73/61 R |

FOREIGN PATENT DOCUMENTS

1302731 1/1973 United Kingdom .

*Primary Examiner*—John Chapman
*Assistant Examiner*—Mark Spector
*Attorney, Agent, or Firm*—Cohen, Pontani & Lieberman

[57] ABSTRACT

A procedure for analyzing air content of a liquid, e.g. pulp slurry, wherein the ratio $I_{att}/I_{sc}$ between ultrasound attenuation and scattered ultrasound attenuation and/or the logarithm $\log (I_{att}/I_{sc})$ is determined. The respective measuring apparatus comprises an ultrasound transmitter (1) and an ultrasound receiver (2) and a scattered ultrasound receiver (3), the latter being disposed to measure members (4) for determining the ratio $I_{att}/I_{sc}$ and/or the logarithm $\log (I_{att}/I_{sc})$.

9 Claims, 2 Drawing Sheets

PROCEDURE AND APPARATUS FOR ANALYZING PULP SLURRY

This is a continuation of U.S. application Ser. No. 137,277, filed Dec. 22, 1987 now abandoned, which is a continuation of U.S. application Ser. No. 915,817 filed Oct. 6, 1986, abandoned.

The present invention concerns a procedure for analysing the air content of a liquid or suspension, e.g. pulp slurry. The invention further concerns apparatus for analysing the air content of a liquid or suspension, e.g. pulp slurry. The object of the invention is to provide a procedure by which the air content of a liquid or suspension, e.g. of pulp slurry, can be determined in the first place by an on-line method from continuous flow, without sampling and/or with sampling.

Furthermore, an object of the invention is to provide a novel apparatus applying the procedure.

Reference is made to the claims section regarding the features which characterize the invention.

Measurement of the characteristics of liquid or suspension, and in particular of pulp slurry, on the basis of ultrasound attenuation is known in the art through the patents: U.S. No. 2,755,662, U.S. No. 3,710,615, U.S. No. 3,914,984 and GB 1,302,731. In these procedures of prior art, analysis is based on determining the attenuation of ultrasound when ultrasound is exponentially attenuated, as a function of its path length, in accordance with formula (I):

$$I_{att} = I_0 e^{-ax}, \quad (I)$$

where $I_{att}$ is the measured, attenuated intensity, $I_0$ is the intensity at the starting point, a is an attenuation constant which is characteristic for each substance, and x is the path length to the point of measurement (the distance which the ultrasound travels in the liquid). The attenuation is linear when plotted in semilogarithmic coordinates.

The invention is based on measurement of the attenuated intensity of ultrasound and of the scattered intensity of ultrasound. The attenuation of scattered ultrasound can be presented by the formula (II).

$$I_{sc} = I_0 e^{-(b-\beta)x}, \quad (II)$$

where $I_{sc}$ is the measured, scattered intensity, $I_0$ is the intensity scattered by the measuring volume in the direction towards the ultrasound beam pick-up, $\beta$ is a constant representing the contribution of scattering to the attenuation of ultrasound, including multiple scattering, and b is the average attenuation constant of the scattering incident on the scattering pick-up from different directions. The ratio of transmission attenuation and scattering attenuation is $$\frac{I_{att}}{I_{sc}} = \frac{I_0 e^{-ax}}{I_0 e^{-(b-\beta)x}} = \text{Const. } e^{-(a-b+\beta)x} \quad (III)$$

We now denote: $\Delta = a - b + \beta$.

The slope $\Delta$ of the linear graphic representation of the logarithm of the ratio between transmission attenuation and scatter indicates the effect of the air content in the liquid, as a function of distance x. We find from formula (III):

$$\frac{I_{att}}{I_{sc}} = \text{Const. } e^{-\Delta \delta_1} \quad (IV)$$

$\delta_1$ is the air content, and $\Delta$ is a calibration constant, associated with the geometry that has been selected, e.g. the pick-up dispositions.

In experiments that have been carried out, the logarithm of the ratio between transmission attenuation and scatter $$\log \frac{I_{att}}{I_{sc}} = -\Delta \delta_1 \quad (V)$$

was found to be linearly dependent on the air content in a great variety of liquids and suspensions. In other words, the slope $\Delta$ of the linear graph is a constant specific to each combination of material and dimensional geometry. When $\log (I_{att}/I_{sc})$ is determined, the air content $\delta_1$ is found by dividing the result of determination by the constant $\Delta$. When $\delta_1$ is zero, a constant value is found for $\log (I_{att}/I_{sc})$, independent of any other characteristics of the liquid or suspension, which include the particle size, temperature, viscosity, etc. However, $\log (I_{att}/I_{sc}) \delta_{1(o)}$ must always be deducted from the value of $\log (I_{att}/I_{sc}) \delta_1$ prior to division by $\Delta 1$.

In constant conditions, substantially constant consistency and substantially constant particle size and/or particle distribution $$\log I_{att} = -\Delta \delta_1 + a \quad (VI)$$

where $a = \log I_{sc}$, i.e. constant.

In this case it is not necessary to determine the scattered intensity at all.

In air-free conditions $$\frac{I_{att}}{I_{sc}} = e^{-\Delta}, \quad (VII)$$

or $$\log \frac{I_{att}}{I_{sc}} = -\Delta \quad (VIII)$$

Figure 2:
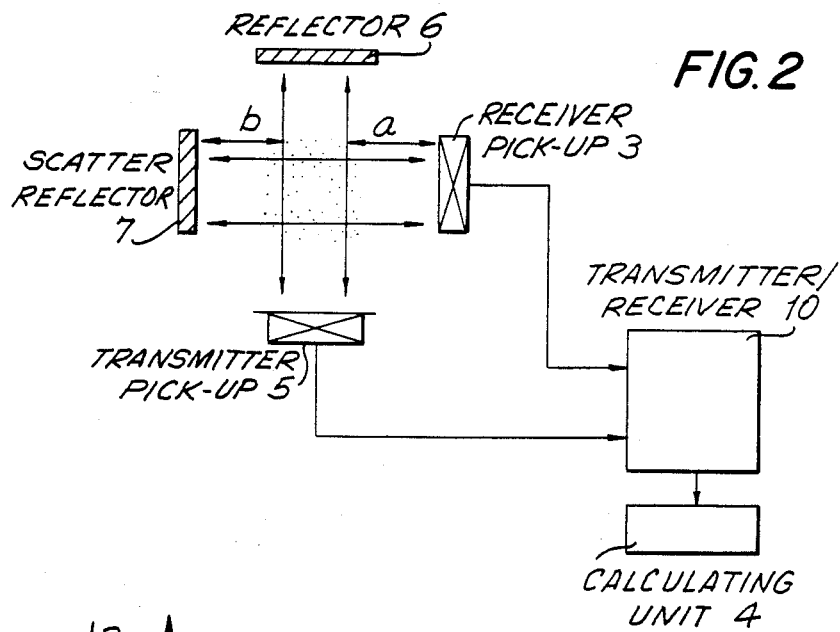
Figure 3:
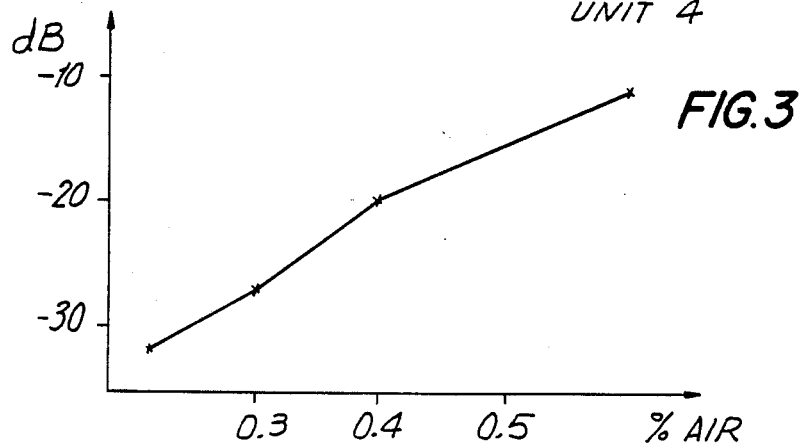
Figure 4:
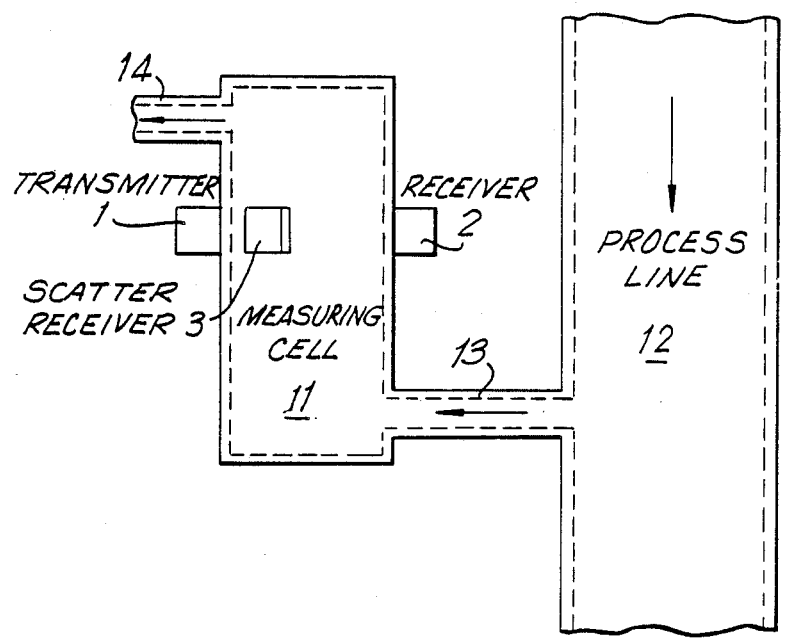
Figure 5:
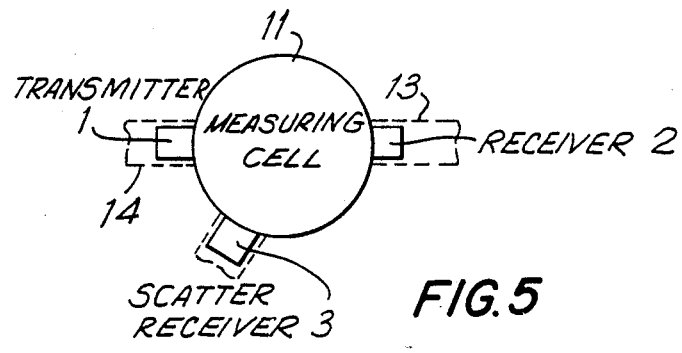

The invention is described in the following, in detail, with the aid of embodiment examples, referring to the attached drawings, wherein:

FIG. 1 presents an arrangement for measurement, according to the invention, in schematic representation, FIG. 2 presents another arrangement for measurement, according to the invention, in schematic representation, FIG. 3 shows, graphically, results from an experiment concerning the ratio of scatter and of ultrasound attenuation, and FIGS. 4–5 show an embodiment of the apparatus of the invention in connection with a process line in side view and in top view, corresp.

In the test arrangement depicted in FIG. 1, an ultrasound transmitter 1 has been disposed to emit an ultrasound beam $R_3$ into the pulp slurry A by action of the pick-up 8. The attenuation of the ultrasound, i.e., the attenuated ultrasound $R_2$, is measured with receiver 2, that is, with a pick-up 9. The attenuation of ultrasound conforms to formula (I).

In FIG. 1 is further seen a scattered ultrasound receiver shown at reference numeral 3 and commonly known as a scatter pick-up, scatter receiver or scatter detector. The scatter detector 3 measures the attenuation $I_{sc}$ of the ultrasound $R_1$. The attenuation of the scattered ultrasound conforms to the formula (II). The scattered ultrasound receiver 3, that is the scatter pick-up, has been placed at a distance from the straight-line path of ultrasound between the transmitter 1, i.e., 1 and attenuation receiver 2 that is, as shown in FIG. 1, scatter detector 3 is not in the straight-line path from transmitter 1 through ultrasound sender or pick-up 3 and attenuation receiver detector 9 to attenuation receiver 2.

In FIG. 1 are further seen the calculation members, i.e., a calculating unit 4, to which the signals derived from the ultrasound receiver and from the scattered ultrasound receiver 3 have been conducted. The calculating unit has been arranged to calculate the ratio $I_{att}/I_{sc}$ according to formula (III) and formula (IV) and/or the logarithm of this ratio.

In FIG. 1, the distances of the ultrasound transmitter pick-up 8 and of the receiver pick-ups 3, 9 from the center of the pulp slurry under measurement, A, are substantially equal (=x). However, if desired, these distances can be selected in an optimal way to account for the characteristics of the substance that is being investigated and the conditions of measurement.

In the measuring arrangement depicted in FIG. 2, the ultrasound transmitter/receiver/scattered ultrasound receiver 1, 2, 3 consits of one single unit 10. The ultrasound transmitter and receiver pick-up 8, 9 consists of a unitary pick-up 5. The apparatus further comprises an ultrasound reflector 6, disposed to reflect the ultrasound emitted by the transmitter/-receiver pick-up 5 back to the same pick-up.

The apparatus depicted in FIG. 2 further comprises a scattered ultrasound receiver 3 and a scatter reflector 7. The scatter reflector 7 has been disposed at a distance (b) from the straight-line path of the ultrasound between the ultrasound transmitter/receiver pick-up 5 and the ultrasound reflector 6, to reflect scattered ultrasound to the scatter receiver pick-up 3, to be further conducted to the ultrasound transmitter/receiver 10. The signals derived from the ultrasound transmitter/receiver 10 have further been carried to the calculating unit 4, for determining the ratio $I_{att}/I_{sc}$ or the logarithm log ($I_{att}/I_{sc}$) according to formulae (III), (IV) and/or formulae (V).

In FIG. 3 is graphically seen the ratio of ultrasound scattering and direct attenuation, as a function of air content, for pine cellulose, the consistency of the pulp slurry being 0.9%. The conditions of experiment were as shown in FIG. 2. The air content of the pulp slurry was measured with an air content measuring apparatus operating on the compression principle. In FIG. 3 has been plotted on the vertical axis the level of the ratio, in decibels, and on the horizontal axis the air content, in percent. According to the results of experiment, the ratio of ultrasound scattering and attenuation is substantially linearly dependent on the air content of the pulp slurry.

In FIGS. 4-5 are seen a measuring cell 11, made of plastic, e.g. plexy, and connected to a process line 12 through pipe line 13 for conducting pulp slurry from said process line to said cell. Pulp slurry is passed away from said cell through outlet 14. An ultrasound transmitter 1 has been clamped on the cell 11 and an ultrasound receiver 2 has been clamped on the opposite side of cell 11. Further a scattered ultrasound receiver 3 has been clamped on cell 11, i.e. receiver 3 is placed at a distance from the straight-line path of ultrasound between the transmitter and the receiver.

The apparatus of FIGS. 4-5 is used as disclosed above. However, in constant conditions, i.e. constant consistency and constant particle size or particle distribution, log $I_{sc}$ is constant, and scattered ultrasound receiver is unnecessary.

The process provided in accordance with the invention is particularly useful for determining the air content of a pulp slurry when the air content is between about 0 and 5 percent and more preferably, between about 0 and 1.5 percent. Furthermore, the pulp slurries with which the process is useful generally contain between about 0 and 2 percent pulp and more preferably, between about 0 and 1.5 percent pulp.

What is claimed is:

1. A procedure for analyzing the air content $\delta_1$ of a liquid or suspension, characterized in that, into the liquid is conducted ultrasound and the attenuation $I_{att}$ and $I_{sc}$ of the ultrasound are measured, and the air content $\delta_1$ of the liquid, is determined by determining the function $$\log \frac{I_{att}}{I_{sc}} = -\Delta\delta_1 \tag{V}$$

where $I_{att}$ is the measured, attenuated intensity, $I_{sc}$ is the measured, scattered intensity and $\Delta$ is a slope constant.

2. Procedure according to claim 1, characterized in that the attenuation values of air-free condition are determined by determining the function $$\frac{I_{att}}{I_{sc}} = e^{-\Delta}, \tag{VII}$$

or $$\log \frac{I_{att}}{I_{sc}} = -\Delta \tag{VIII}$$

3. An apparatus for analyzing the air content $\delta_i$ of a liquid or suspension comprising:
an ultrasound transmitter (1);
an attenuation ultrasound receiver (2) for measuring the attenuation of ultrasound, $I_{att}$;
a scattered ultrasound receiver (3) disposed to measure the attenuation, $I_{mc}$, of scattered ultrasound; and
calculating means (4) for determining at least one of the ratio $I_{att}/I_{mc} = e^{-\Delta\delta_i}$; (1)

and $\log (I_{att}/I_{mc}) = -\Delta\delta_i$; (2)

wherein $\Delta$ is a slope coefficient.

4. An apparatus according to claim 3, wherein the ultrasound transmitter (1) and the attenuation ultrasound receiver (2) are not the same unit and the scattered ultrasound receiver (3) is disposed at a distance, c, from the straight line path between the ultrasound transmitter (1) and the attenuation ultrasound receiver (2).

5. An apparatus according to claim 3, wherein the ultrasound transmitter (1) and the attenuation ultrasound receiver (2) are the same unit.

6. An apparatus according to claim 5, wherein the apparatus further comprises a attenuation receiver detector (9) and an ultrasound attenuation reflector (6), said reflector (6) being disposed to reflect the ultrasound emitted by the attenuation receiver detector (9) back to itself.

7. An apparatus according to claim 5, wherein the apparatus further comprises a scatter reflector (7) arranged so as to reflect scattered ultrasound back to the scattered ultrasound receiver (3).

8. An apparatus according to claim 6, wherein the apparatus further comprises a scatter reflector (7) arranged so as to reflect scattered ultrasound back to the scattered ultrasound receiver (3).

9. An apparatus according to claim 8, wherein the attenuation receiver detector (9), ultrasound attenuation reflector (6), scatter reflector (7) and scattered ultrasound receiver (3) are arranged in such a way that the straight line path of ultrasound between the attenuation receiver detector (9) and ultrasound attenuation reflector (6) is substantially perpendicular to the straight line path of scattered ultrasound between scatter reflector (7) and scattered ultrasound receiver (3).

* * * * *